US012773350B2

(12) United States Patent

Dick et al.

(10) Patent No.: US 12,773,350 B2

(45) Date of Patent: Oct. 27, 2026

(54) METHODS AND SYSTEMS FOR PERFORMING A POSTERIOR CAPSULOTOMY AND FOR LASER EYE SURGERY WITH A PENETRATED CORNEA

(71) Applicant: AMO Development, LLC, Irvine, CA (US)

(72) Inventors: H. Burkhard Dick, Bochum (DE); David Scott, Oakland, CA (US)

(73) Assignee: AMO Development, LLC, Irvine, CA (US)

( * ) Notice: Subject to any disclaimer, the term of this patent is extended or adjusted under 35 U.S.C. 154(b) by 177 days.

(21) Appl. No.: 18/755,600

(22) Filed: Jun. 26, 2024

(65) Prior Publication Data

US 2024/0342005 A1 Oct. 17, 2024

Related U.S. Application Data

(62) Division of application No. 17/810,298, filed on Jun. 30, 2022, now abandoned, which is a division of application No. 16/208,429, filed on Dec. 3, 2018, now Pat. No. 11,376,158, which is a division of application No. 14/020,640, filed on Sep. 6, 2013, now Pat. No. 10,143,590.

(60) Provisional application No. 61/699,204, filed on Sep. 10, 2012, provisional application No. 61/698,516, filed on Sep. 7, 2012.

(51) Int. Cl.

*A61F 9/008* (2006.01)
*A61F 9/009* (2006.01)

(52) U.S. Cl.

CPC .......... *A61F 9/008* (2013.01); *A61F 9/00825* (2013.01); *A61F 9/009* (2013.01); *A61F 2009/00844* (2013.01); *A61F 2009/00851* (2013.01); *A61F 2009/0087* (2013.01); *A61F 2009/00872* (2013.01); *A61F 2009/00887* (2013.01); *A61F 2009/00889* (2013.01)

(58) Field of Classification Search

None

See application file for complete search history.

(56) References Cited

U.S. PATENT DOCUMENTS 4,676,793 A 6/1987 Bechert, II
4,773,415 A 9/1988 Tan (Continued)

OTHER PUBLICATIONS

Menapace R., et al., Posterior Optic Buttonholing: Rationale, Surgical Technique and Pearls. American Academy of Ophthalmology[online]. [retrieved on Oct. 14, 2010] Retrieved from the Internat URL: https://www.aao.org/current-insight!posterior-optic-buttonholing-rationale-surgical-te.

(Continued)

*Primary Examiner* — Michael W Kahelin

(57) ABSTRACT

Method and apparatus for performing a laser-assisted posterior capsulotomy and for performing laser eye surgery on an eye having a penetrated cornea are provided. A method for performing a posterior capsulotomy includes injecting fluid between the lens posterior capsule and the anterior hyaloids membrane to separate the lens posterior capsule and the anterior hyaloids membrane. With the lens posterior capsule separated from the anterior hyaloids membrane, a posterior capsulotomy is performed on the lens posterior capsule by using a laser to incise the lens posterior capsule.

6 Claims, 8 Drawing Sheets

(56) References Cited

U.S. PATENT DOCUMENTS

| | | | |
|---|---|---|---|
| 4,819,617 | A | 4/1989 | Goldberg et al. |
| 5,098,444 | A | 3/1992 | Feaster |
| 5,459,570 | A | 10/1995 | Swanson et al. |
| 5,720,894 | A | 2/1998 | Neev et al. |
| 5,748,352 | A | 5/1998 | Hattori |
| 5,748,898 | A | 5/1998 | Ueda |
| 5,957,915 | A | 9/1999 | Trost |
| 5,984,916 | A | 11/1999 | Lai |
| 6,019,472 | A | 2/2000 | Koester et al. |
| 6,053,613 | A | 4/2000 | Wei et al. |
| 6,111,645 | A | 8/2000 | Tearney et al. |
| 6,165,190 | A | 12/2000 | Nguyen |
| 6,454,761 | B1 | 9/2002 | Freedman |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 2002/0123744 | A1 * | 9/2002 | Reynard ............... A61F 9/0079 606/167 |
| 2003/0158543 | A1 * | 8/2003 | Van Saarloos ...... A61F 9/00804 606/5 |
| 2003/0187501 | A1 | 10/2003 | Okada |
| 2007/0123981 | A1 | 5/2007 | Tassignon |
| 2008/0269888 | A1 | 10/2008 | Malyugin |
| 2009/0012507 | A1 | 1/2009 | Culbertson et al. |
| 2009/0137991 | A1 | 5/2009 | Kurtz |
| 2009/0171327 | A1 | 7/2009 | Kurtz et al. |
| 2010/0324543 | A1 * | 12/2010 | Kurtz ...................... A61F 9/008 606/6 |
| 2011/0172649 | A1 | 7/2011 | Schuele et al. |
| 2011/0178512 | A1 | 7/2011 | Blumenkranz et al. |
| 2011/0184392 | A1 | 7/2011 | Culbertson et al. |
| 2011/0196350 | A1 | 8/2011 | Friedman et al. |
| 2011/0202046 | A1 | 8/2011 | Angeley et al. |
| 2011/0319873 | A1 | 12/2011 | Raksi et al. |
| 2011/0319875 | A1 | 12/2011 | Loesel et al. |
| 2012/0069298 | A1 | 3/2012 | Ng |
| 2012/0078241 | A1 * | 3/2012 | Gooding ................. A61F 9/009 606/6 |
| 2012/0197102 | A1 | 8/2012 | Hanebuchi et al. |
| 2013/0103012 | A1 | 4/2013 | Grant et al. |
| 2014/0074074 | A1 | 3/2014 | Dick et al. |
| 2014/0128731 | A1 | 5/2014 | Gonzalez et al. |
| 2015/0202085 | A1 | 7/2015 | Lemonis et al. |

OTHER PUBLICATIONS

Menapace R., "Posterior Capsulorhexis Combined with Optic Buttonholing: An Alternative to Standard in-the-Bag Implantation of Sharp-Edged Intraocular Lenses? A Critical Analysis of 1000 Consecutive Cases," Graefe's Archive for Clinical and Experimental Ophthalmology, 2008, vol. 246 (6), pp. 787-801.

Todd F. D., "Cataract Surgery: Phacoemulsification and IOL (Intraocular Lens) Implant Surgery," YouTube, Surgery by Dr. Todd Fladen of The Fladen Eye and Lasik Center, Apr. 23, 2011, https://www.youtube.com/watchv=t80JvhMOjws (Year: 2011), 2 pages.

Worst J.G.F., et al., "Cisternal Anatomy of the Vitreous," in: British Journal ofOphthalmology, 1995, Kugler Publications, 110.

* cited by examiner

METHODS AND SYSTEMS FOR PERFORMING A POSTERIOR CAPSULOTOMY AND FOR LASER EYE SURGERY WITH A PENETRATED CORNEA

CROSS-REFERENCE

This application is a divisional of and claims priority to U.S. patent application Ser. No. 17/810,298, filed Jun. 30, 2022, which is a divisional of and claims priority to U.S. patent application Ser. No. 16/208,429, filed Dec. 3, 2018, now U.S. Pat. No. 11,376,158, which is a divisional of and claims priority to U.S. patent application Ser. No. 14/020,640, filed September 6. 2013, now U.S. Pat. No. 10,143,590, which claims the benefit of U.S. Provisional Application No. 61/698,516, filed Sep. 7, 2012, and U.S. Provisional Application No. 61/699,204, filed Sep. 10, 2012. The above applications are incorporated herein by reference in their entirety.

BACKGROUND

Cataract extraction is one of the most commonly performed surgical procedures in the world. A cataract is formed by opacification of the crystalline lens or its envelope—the lens capsule—of the eye. A cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical maneuvers, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate its removal through an opening made in the lens anterior capsule. The nucleus of the lens is contained within an outer membrane of the lens that is referred to as the lens capsule. Access to the lens nucleus can be provided by performing an anterior capsulotomy in which an opening is formed in the anterior side of the lens capsule. Access to the lens nucleus can also be provided by performing a manual continuous curvilinear capsulorhexis (CCC) procedure, which has been recently developed. After removal of the lens nucleus, a synthetic foldable intraocular lens (IOL) can be inserted into the remaining lens capsule of the eye through a small incision. Typically, the IOL is held in place by the lens anterior capsule. The IOL may also be held by the lens posterior capsule, either alone or in unison with the lens anterior capsule. This latter configuration is known in the field as a "bag-in-lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the lens anterior capsule in a circular fashion followed by the removal of a circular fragment of lens anterior capsule typically in the range of 5-8 mm in diameter. The smaller the capsulotomy, the more difficult it is to produce manually. The capsulotomy facilitates the next step of nuclear sculpting by phacoemulsification.

Due to a variety of complications associated with the initial can-opener technique, attempts were made by leading experts in the field to develop a better technique for forming an opening in the lens anterior capsule preceding the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the lens anterior capsule provides both a clear central access for tool insertion during removal of the nucleus and for IOL insertion, a permanent aperture for transmission of the image to the retina by the patient, and also support of the IOL inside the remaining capsule that limits the potential for dislocation. The resulting reliance on the shape, symmetry, uniformity, and strength of the remaining capsule to contain, constrain, position, and maintain the IOL in the patient's eye limits the placement accuracy of the IOL, both initially and over time. Subsequently, a patient's refractive outcome and resultant visual acuity are less deterministic and intrinsically sub-optimal due to the IOL placement uncertainty. This is especially true for astigmatism correcting ("toric") and accommodating ("presbyopic") IOLs.

Problems may also develop related to inability of the surgeon to adequately visualize the lens capsule due to lack of red reflex, to grasp the lens capsule with sufficient security, and to tear a smooth circular opening in the lens capsule of the appropriate size and in the correct location without creating radial rips and extensions. Also present are technical difficulties related to maintenance of the depth of the anterior chamber after opening the lens capsule, small pupil size, and/or the absence of a red reflex due to lens opacity. Some of the problems with visualization can be minimized through the use of dyes such as methylene blue or indocyanine green. Additional complications may also arise in patients with weak zonules (typically older patients) and very young children that have very soft and elastic capsules, which are very difficult to controllably and reliably rupture and tear.

The implantation of a "bag-in-lens" IOL typically uses anterior and posterior openings in the lens capsule of the same size. Manually creating matching capsulotomies for the "bag-in-lens" configuration, however, is particularly difficult.

Many cataract patients have astigmatic visual errors. Astigmatism can occur when the corneal curvature is unequal in all directions. IOLs can be used to correct for astigmatism but require precise rotational and central placement. Additionally, IOLs are not typically used for correction beyond 5D of astigmatism. Many patients, however, have astigmatic visual errors exceeding 5D. Higher correction beyond 5D typically requires reshaping the cornea to make it more spherical. There are numerous existing approaches for reshaping the cornea, including Corneaplasty, Astigmatic Keratotomy, Corneal Relaxing Incision (CRI), and Limbal Relaxing Incision (LRI). In Astigmatic Keratotomy, Corneal Relaxing Incision (CRI), and Limbal Relaxing Incision (LRI), corneal incisions are made in a well-defined manner and depth to allow the cornea to change shape to become more spherical. Presently, these corneal incisions are typically accomplished manually often with limited precision.

Thus, improved methods and systems for treating cataracts are needed.

SUMMARY

Methods and apparatus for performing a posterior capsulotomy and for performing laser eye surgery with a penetrated cornea are disclosed. The disclosed methods provide for the formation of precise openings in the anterior and posterior sides of the lens capsule, thereby preparing the lens capsule to receive a replacement lens (e.g., a "bag-in-lens" lens, or any other suitable lens including an existing IOL). And the disclosed methods for performing laser eye surgery with a penetrated cornea can be used, for example, to treat an eye having a pupil that does not dilate sufficiently to provide adequate surgical access.

In one aspect, a method is provided for performing laser-assisted cataract surgery on an eye having a lens posterior capsule and an anterior hyaloid membrane. The method includes injecting fluid between the lens posterior capsule and the anterior hyaloid membrane to separate the lens posterior capsule and the anterior hyaloid membrane. With the lens posterior capsule separated from the anterior hyaloid membrane, a posterior capsulotomy is performed on the lens posterior capsule by using a laser to incise the lens posterior capsule. The fluid can be injected into the Berger's space of the eye. In many embodiments, the fluid is an ophthalmic viscosurgical device (OVD). In many embodiments, the posterior capsulotomy leaves the anterior hyaloid membrane completely intact.

The posterior capsulotomy can be performed using any suitable parameters. For example, the posterior capsulotomy can be performed using an incision depth between 400 μm and 800 μm. In many embodiments, the posterior capsulotomy is performed using pulse energy between 7 μJ and 10 μJ. In many embodiments, the posterior capsulotomy is performed using a capsulotomy diameter of at least 3.5 mm.

The method for performing laser-assisted cataract surgery on an eye having a lens posterior capsule and an anterior hyaloid membrane can include one or more additional acts. For example, the method can include installing a replacement lens so that the replacement lens is at least partially constrained by the lens capsule. For example, the replacement lens can be installed using a posterior optic buttonholing technique. As another example, the replacement lens can be installed using a bag-in-lens technique. The method can include performing an anterior capsulotomy on the lens capsule by using a laser to incise the lens capsule. The method can include removing at least a portion of the lens nucleus.

In another aspect, a method is provided for performing laser eye surgery on an eye having a cornea. The method includes coupling an eye having a penetration through the cornea to a laser surgery system by using a liquid interface disposed between the cornea and the laser surgery system, and forming one or more incisions in the eye by using the laser surgery system to transmit light through the liquid interface.

The method for performing laser eye surgery on an eye having a cornea can include additional acts. For example, the method can include forming the penetration through the cornea. The method can include inserting an iris-expanding device through the penetration in the cornea.

In another aspect, a system is provided for performing laser-assisted cataract surgery on an eye having an anterior chamber. The system includes a laser configured to generate a laser beam comprising a plurality of laser pulses, a scanning assembly configured to scan a focal point of the laser beam within the eye to incise eye tissue, and a controller configured to scan the focal point to incise eye tissue so as to account for at least one optical characteristic of an OVD in the anterior chamber to determine one or more control parameters used to control scanning of the focal point.

In many embodiments, the system for performing laser-assisted cataract surgery on an eye having an anterior chamber further includes an imaging device configured to generate output in response to imaging the eye. In many embodiments, the controller is configured to process output from the imaging device to determine dimensional attributes of the anterior chamber and use the dimensional attributes of the anterior chamber in conjunction with an index of refraction for the OVD disposed in the anterior chamber to operate the scanning assembly to scan the focal point to incise eye tissue so as to account for the at least one optical characteristic of the OVD.

In another aspect, a method is provided for performing laser-assisted cataract surgery on an eye having an anterior chamber. The method includes generating a laser beam comprising a plurality of pulses, and scanning a focal point of the laser beam within the eye to incise tissue of the eye disposed posterior to the anterior chamber so as to account for at least one optical characteristic of an OVD disposed in the anterior chamber to determine one or more control parameters used to control scanning of the focal point. In many embodiments, the OVD has an index of refraction and the accounted for at least one optical characteristic of the OVD includes the index of refraction.

In many embodiments, the method includes processing output from an imaging device to determine dimensional attributes of the anterior chamber. The dimensional attributes of the anterior chamber are used in conjunction with the index of refraction of the OVD to operate the scanning assembly to scan the focal point to incise eye tissue so as to account for the at least one optical characteristic of the OVD.

In another aspect, a method is provided for performing a laser-assisted posterior capsulotomy on a lens posterior capsule of an eye. The method includes injecting fluid between a replacement lens and the lens posterior capsule to separate the lens posterior capsule and the replacement lens, and performing a posterior capsulotomy on the lens posterior capsule by using a laser to incise the lens posterior capsule. In many embodiments, the injected fluid is an OVD.

The method for performing a laser-assisted posterior capsulotomy on a lens posterior capsule of an eye can include one or more additional acts. For example, the method can include injecting fluid between the lens posterior capsule and an anterior hyaloid membrane of the eye to separate the lens posterior capsule and the anterior hyaloid membrane. In many embodiments, the posterior capsulotomy leaves the anterior hyaloid membrane completely intact.

The posterior capsulotomy can be performed using any suitable parameters. For example, the posterior capsulotomy can be performed using an incision depth between 400 μm to 800 μm. The posterior capsulotomy can be performed using pulse energy between 7 μJ to 10 μJ. The posterior capsulotomy can be performed using a capsulotomy diameter of at least 3.5 mm.

In many embodiments, performing the posterior capsulotomy includes compensating for the presence of the replacement lens. For example, performing the posterior capsulotomy can include using an index of refraction for the replacement lens to determine control parameters used to scan the laser to incise the lens posterior capsule.

In many embodiments, the method for performing a laser-assisted posterior capsulotomy on a lens posterior capsule of an eye includes one or more additional acts. For example, the method can include performing an anterior capsulotomy on the lens capsule by using a laser to incise the lens capsule, removing at least a portion of the lens nucleus, and installing the replacement lens so that the replacement lens is at least partially constrained by the lens capsule having the anterior capsulotomy.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
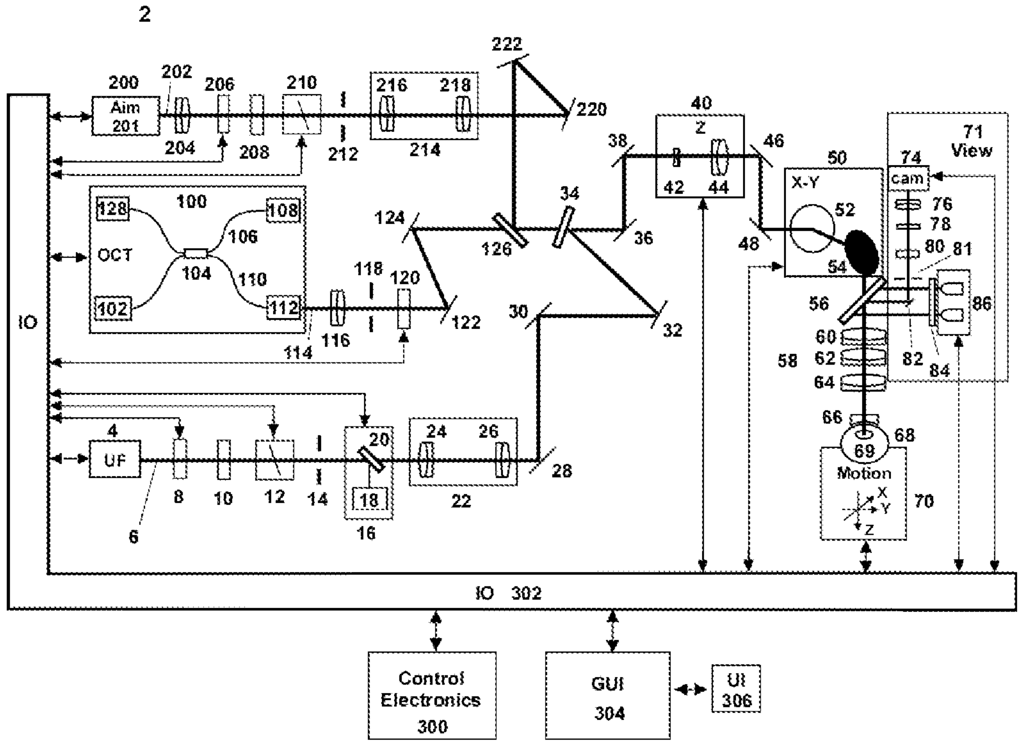
FIG. 1 shows a schematic representation of an embodiment of a system that can be used to perform a posterior capsulotomy and to perform surgery on an eye having a penetrated cornea.

The present invention can be implemented by a system that projects or scans an optical beam into a patient's eye 68, such as system 2 shown in FIG. 1. System 2 includes an ultrafast (UF) light source 4 (e.g., a femtosecond laser). Using system 2, a beam can be scanned in the patient's eye 68 in three dimensions: X, Y, Z. Short-pulsed laser light can be focused into eye tissue to produce dielectric breakdown to cause photodisruption around the focal point (the focal zone), thereby rupturing the tissue in the vicinity of the photo-induced plasma. In this embodiment, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability bound the lower limit for pulse energy and repetition rate. The peak power of the focused spot in the eye 68 and specifically within the crystalline lens 69 and lens anterior capsule of the eye is sufficient to produce optical breakdown and initiate a plasma-mediated ablation process. Near-infrared wavelengths are preferred because linear optical absorption and scattering in biological tissue is reduced for near-infrared wavelengths. As an example, laser 4 can be a repetitively pulsed 1035 nm device that produces 500 fs pulses at a repetition rate of 100 kHz and individual pulse energy in a suitable range (e.g., from 7 to 10 microjoule).

The laser 4 is controlled by control electronics 300, via an input and output device 302, to create optical beam 6. Control electronics 300 may be a computer, microcontroller, etc. In this example, the controller 300 controls the entire system and data is moved through input/output device IO

302. A graphical user interface GUI 304 can be used to set system operating parameters, process user input (UI) 306, and display gathered information such as images of ocular structures.

The generated UF light beam 6 proceeds towards the patient eye 68 passing through a half-wave plate 8 and a linear polarizer, 10. The polarization state of the beam can be adjusted so that the desired amount of light passes through the half-wave plate 8 and the linear polarizer 10, which together act as a variable attenuator for the UF beam 6. Additionally, the orientation of the linear polarizer 10 determines the incident polarization state incident upon a beam combiner 34, thereby optimizing the beam combiner 34 throughput.

The UF light beam 6 proceeds through a system-controlled shutter 12, an aperture 14, and a pickoff device 16. The system-controlled shutter 12 ensures on/off control of the laser for procedural and safety reasons. The aperture 14 sets an outer useful diameter for the UF light beam 6 and the pickoff device 16 monitors the resulting beam. The pickoff device 16 includes a partially reflecting mirror 20 and a detector 18. Pulse energy, average power, or a combination can be measured using the detector 18. Output from the detector 18 can be used for feedback to the half-wave plate 8 for attenuation and to verify whether the system-controlled shutter 12 is open or closed. In addition, the system-controlled shutter 12 can have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a two-element beam expanding telescope comprised of spherical optics 24, 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the beam conditioning stage 22 can be used to image aperture 14 to a desired location (e.g., the center location between a 2-axis scanning device 50 described below). In this way, the amount of light that makes it through the aperture 14 is assured to make it through the scanning system. The pickoff device 16 is then a reliable measure of the usable light.

After exiting the beam conditioning stage 22, the beam 6 reflects off of fold mirrors 28, 30, 32. These mirrors can be adjustable for alignment purposes. The beam 6 is then incident upon the beam combiner 34. The beam combiner 34 reflects the UF beam 6 (and transmits both the imaging, in this exemplary case, an optical coherence tomography (OCT) beam 114, and an aim 202 beam described below). For efficient beam combiner operation, the angle of incidence is preferably kept below 45 degrees and the polarization of the beams is fixed where possible. For the UF beam 6, the orientation of the linear polarizer 10 provides fixed polarization. Although OCT is used as the imaging modality in this non-limiting example, other approaches, such as Purkinje imaging, Scheimpflug imaging, confocal or non-linear optical microscopy, fluorescence imaging, ultrasound, structured light, stereo imaging, or other known ophthalmic or medical imaging modalities and/or combinations thereof may be employed.

Following the beam combiner 34, the beam 6 continues onto a z-adjust or Z scan device 40. In this illustrative example the z-adjust 40 includes a Galilean telescope with two lens groups 42, 44 (each lens group includes one or more lenses). The lens group 42 moves along the z-axis about the collimation position of the telescope. In this way, the focus position of the spot in the patient's eye 68 moves along the z-axis as indicated. In general, there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, the lens group 44 could be moved along the z-axis to actuate the z-adjust, and scan. The z-adjust 40 is the z-scan device for treatment in the eye 68. It can be controlled automatically and dynamically by the system and selected to be independent or to interplay with the X-Y scan device described next. The mirrors 36, 38 can be used for aligning the optical axis with the axis of the z-adjust device 40.

After passing through the z-adjust device 40, the beam 6 is directed to the x-y scan device 50 by mirrors 46, 48. The mirrors 46, 48 can be adjustable for alignment purposes. X-Y scanning is achieved by the scanning device 50 preferably using two mirrors 52, 54 under the control of the control electronics 300, which rotate in orthogonal directions using motors, galvanometers, or any other well known optic moving device. The mirrors 52, 54 are located near the telecentric position of an objective lens 58 and a liquid optical interface 66 combination described below. Tilting the mirrors 52, 54 changes the resulting direction of the beam 6, causing lateral displacements in the plane of UF focus located in the patient's eye 68. The objective lens 58 may be a complex multi-element lens element, as shown, and represented by lenses 60, 62, and 64. The complexity of the objective lens 58 will be dictated by the scan field size, the focused spot size, the available working distance on both the proximal and distal sides of objective lens 58, as well as the amount of aberration control. An f-theta objective lens 58 of focal length 60 mm generating a spot size of 10 μm, over a field of 10 mm, with an input beam size of 15 mm diameter is an example. Alternatively, X-Y scanning by the scanning device 50 may be achieved by using one or more moveable optical elements (e.g., lenses, gratings), which also may be controlled by the control electronics 300, via the input and output device 302.

The scanning device 50 under the control of the control electronics 300 can automatically generate the aiming and treatment scan patterns. Such patterns may be comprised of a single spot of light, multiple spots of light, a continuous pattern of light, multiple continuous patterns of light, and/or any combination of these. In addition, the aiming pattern (using the aim beam 202 described below) need not be identical to the treatment pattern (using the light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

The liquid optical interface 66, which can include any suitable ophthalmic lens, can be used to help further focus the light beam 6 into the patient's eye 68 while helping to stabilize eye position. The positioning and character of the light beam 6 and/or the scan pattern the light beam 6 forms on the eye 68 may be further controlled by use of an input device such as a joystick, or any other appropriate user input device (e.g., GUI 304) to position the patient and/or the optical system.

The UF laser 4 and the control electronics 300 can be set to target the targeted structures in the eye 68 and ensure that the light beam 6 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, or other known ophthalmic or medical imaging modalities, such as those mentioned above, and/or combinations thereof. In the embodiment of FIG. 1, an OCT device 100 is described, although other modalities are within the scope of the present invention. An OCT scan of the eye will provide information about the axial location of the lens anterior and posterior capsule, the boundaries of the cataract nucleus, as well as the depth of the anterior chamber. This information is then loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs a time domain detection technique, a frequency detection technique, or a single point detection technique. In FIG. 1, a frequency domain technique is used with an OCT wavelength of 920 nm and bandwidth of 100 nm.

After exiting the connector 112, the OCT beam 114 is collimated using a lens 116. The size of the collimated OCT beam 114 is determined by the focal length of the lens 116. The size of the beam 114 is dictated by the desired NA at the focus in the eye and the magnification of the beam train leading to the eye 68. Generally, the OCT beam 114 does not require as high an NA as the UF light beam 6 in the focal plane and therefore the OCT beam 114 is smaller in diameter than the UF light beam 6 at the beam combiner 34 location. Following the collimating lens 116 is an aperture 118, which further modifies the resultant NA of the OCT beam 114 at the eye. The diameter of the aperture 118 is chosen to optimize OCT light incident on the target tissue and the strength of the return signal. A polarization control element 120, which may be active or dynamic, is used to compensate for polarization state changes. The polarization state changes may be induced, for example, by individual differences in corneal birefringence. 122, 124 are then used to direct the OCT beam 114 towards beam combiners 126, 34. Mirrors 122, 124 can be adjustable for alignment purposes and in particular for overlaying of the OCT beam 114 to the UF light beam 6 subsequent to the beam combiner 34. Similarly, the beam combiner 126 is used to combine the OCT beam 114 with the aim beam 202 as described below.

Once combined with the UF light beam 6 subsequent to beam combiner 34, the OCT beam 114 follows the same path as the UF light beam 6 through the rest of the system. In this way, the OCT beam 114 is indicative of the location of the UF light beam 6. The OCT beam 114 passes through the z-scan 40 and x-y scan 50 devices then the objective lens 58, the liquid optical interface 66, and on into the eye 68. Reflections and scatter off of structures within the eye provide return beams that retrace back through the optical system, into the connector 112, through the coupler 104, and to the OCT detector 128. These return back reflections provide OCT signals that are in turn interpreted by the system as to the location in X, Y, and Z of UF light beam 6 focal location.

The OCT device 100 works on the principle of measuring differences in optical path length between its reference and sample arms. Therefore, passing the OCT beam 114 through the z-adjust device 40 does not extend the z-range of the OCT system 100 because the optical path length does not change as a function of movement of the lens group 42. The OCT system 100 has an inherent z-range that is related to the detection scheme, and in the case of frequency domain detection it is specifically related to the spectrometer and the location of the reference arm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust device 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y, and Z should be conducted in order to match the OCT signal information to the UF focus location and also to the relative to absolute dimensional quantities.

Observation of an aim beam may also be used to assist the user to directing the UF laser focus. Additionally, an aim beam visible to the unaided eye in lieu of the infrared OCT beam and the UF light beam can be helpful with alignment provided the aim beam accurately represents the infrared beam parameters. An aim subsystem 200 is employed in the configuration shown in FIG. 1. The aim beam 202 is generated by an aim beam light source 201, such as a helium-neon laser operating at a wavelength of 633 nm. Alternatively a laser diode in the 630-650 nm range can be used. An advantage of using the helium neon 633 nm beam is its long coherence length, which would enable the use of the aim path as a laser unequal path-length interferometer (LUPI) to measure the optical quality of the beam train, for example.

Once the aim beam light source 201 generates the aim beam 202, the aim beam 202 is collimated using a lens 204. The size of the collimated beam is determined by the focal length of the lens 204. The size of the aim beam 202 is dictated by the desired NA at the focus in the eye and the magnification of the beam train leading to the eye 68.

Generally, the aim beam 202 should have close to the same NA as the UF light beam 6 in the focal plane and therefore the aim beam 202 is of similar diameter to the UF light beam 6 at the beam combiner 34. Because the aim beam 202 is meant to stand-in for the UF light beam 6 during system alignment to the target tissue of the eye, much of the aim path mimics the UF path as described previously. The aim beam 202 proceeds through a half-wave plate 206 and a linear polarizer 208. The polarization state of the aim beam 202 can be adjusted so that the desired amount of light passes through the polarizer 208. The half-wave plate 206 and the linear polarizer 208 therefore act as a variable attenuator for the aim beam 202. Additionally, the orientation of polarizer 208 determines the incident polarization state incident upon the beam combiners 126, 34, thereby fixing the polarization state and allowing for optimization of the throughput of the beam combiners 126, 34. Of course, if a semiconductor laser is used as the aim beam light source 200, the drive current can be varied to adjust the optical power.

The aim beam 202 proceeds through a system-controlled shutter 210 and an aperture 212. The system-controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of the polarizer 206.

The aim beam 202 next passes through a beam-conditioning device 214. Beam parameters such as beam diameter, divergence, circularity, and astigmatism can be modified using one or more well known beaming conditioning optical elements. In the case of the aim beam 202 emerging from an optical fiber, the beam-conditioning device 214 can simply include a beam-expanding telescope with two optical elements 216, 218 in order to achieve the intended beam size and collimation. The final factors used to determine the aim beam parameters such as degree of collimation are dictated by what is necessary to match the UF light beam 6 and the aim beam 202 at the location of the eye 68. Chromatic differences can be taken into account by appropriate adjustments of the beam conditioning device 214. In addition, the optical system 214 is used to image aperture 212 to a desired location such as a conjugate location of the aperture 14.

The aim beam 202 next reflects off of fold mirrors 220, 222, which are preferably adjustable for alignment registration to the UF light beam 6 subsequent to the beam combiner 34. The aim beam 202 is then incident upon the beam combiner 126 where the aim beam 202 is combined with the OCT beam 114. The beam combiner 126 reflects the aim beam 202 and transmits the OCT beam 114, which allows for efficient operation of the beam combining functions at both wavelength ranges. Alternatively, the transmit function and the reflect function of the beam combiner 126 can be reversed and the configuration inverted. Subsequent to the beam combiner 126, the aim beam 202 along with the OCT beam 114 is combined with the UF light beam 6 by the beam combiner 34.

A device for imaging the target tissue on or within the eye 68 is shown schematically in FIG. 1 as an imaging system 71. The imaging system 71 includes a camera 74 and an illumination light source 86 for creating an image of the target tissue. The imaging system 71 gathers images that may be used by the control electronics 300 for providing pattern centering about or within a predefined structure. The illumination light source 86 is generally broadband and incoherent. For example, the light source 86 can include multiple LEDs as shown. The wavelength of the illumination light source 86 is preferably in the range of 700 nm to 750 nm, but can be anything that is accommodated by a beam combiner 56, which combines the viewing light with the beam path for the UF light beam 6 and the aim beam 202 (beam combiner 56 reflects the viewing wavelengths while transmitting the OCT and UF wavelengths). The beam combiner 56 may partially transmit the aim wavelength so that the aim beam 202 can be visible to the viewing camera 74. An optional polarization element 84 in front of the light source 86 can be a linear polarizer, a quarter wave plate, a half-wave plate or any combination, and is used to optimize signal. A false color image as generated by the near infrared wavelength is acceptable.

The illumination light from the light source 86 is directed down towards the eye using the same objective lens 58 and the liquid optical interface 66 as the UF light beam 6 and the aim beam 202. The light reflected and scattered off of various structures in the eye 68 are collected by the same lenses 58, 66 and directed back towards the beam combiner 56. At the beam combiner 56, the return light is directed back into the viewing path via beam combiner 56 and a mirror 82, and on to the viewing camera 74. The viewing camera 74 can be, for example but not limited to, any silicon based detector array of the appropriately sized format. A video lens 76 forms an image onto the camera's detector array while optical elements 80, 78 provide polarization control and wavelength filtering respectively. An aperture or iris 81 provides control of imaging NA and therefore depth of focus and depth of field. A small aperture provides the advantage of large depth of field that aids in the patient docking procedure. Alternatively, the illumination and camera paths can be switched. Furthermore, the aim light source 200 can be made to emit infrared light that would not be directly visible, but could be captured and displayed using the imaging system 71.

Coarse adjust registration is usually needed so that when the liquid optical interface 66 is coupled with the eye 68, the targeted structures are in the capture range of the X, Y scan of the system. Therefore a docking procedure is preferred, which preferably takes in account patient motion as the system approaches the contact condition (i.e. contact between the patient's eye 68 and the liquid optical interface 66). The viewing system 71 is configured so that the depth of focus is large enough such that the patient's eye 68 and other salient features may be seen before the liquid optical interface 66 makes contact with the eye 68.

Preferably, a motion control system 70 is integrated into the overall system 2, and may move the patient, the system 2 or elements thereof, or both, to achieve accurate and reliable contact between the liquid optical interface 66 and the eye 68. Furthermore, a vacuum suction subsystem and flange may be incorporated into the system 2, and used to stabilize the eye 68. Alignment of the eye 68 to the system 2 via the liquid optical interface 66 can be accomplished while monitoring the output of the imaging system 71, and performed manually or automatically by analyzing the images produced by the imaging system 71 electronically by means of the control electronics 300 via the IO 302. Force and/or pressure sensor feedback can also be used to discern contact, as well as to initiate the vacuum subsystem. An alternate patient interface can also be used, such as that described in U.S. patent application Ser. No. 13/225,373, which is incorporated herein by reference.

Figure 2:
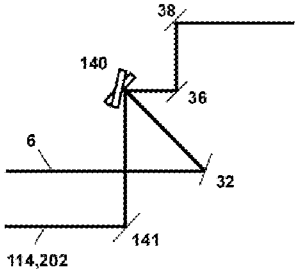
FIG. 2 shows a schematic representation of aspects of another embodiment of a system that can be used to perform a posterior capsulotomy and to perform surgery on an eye having a penetrated cornea.

An alternative beam combining configuration is shown in the alternate embodiment of FIG. 2. For example, the passive beam combiner 34 in FIG. 1 can be replaced with an active combiner 140 as shown in FIG. 2. The active beam combiner 140 can be a moving or dynamically controlled element such as a galvanometric scanning mirror, as shown. The active combiner 140 changes its angular orientation in order to direct either the UF light beam 6 or the combined aim and OCT beams 202,114 towards the scanner 50 and eventually towards the eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
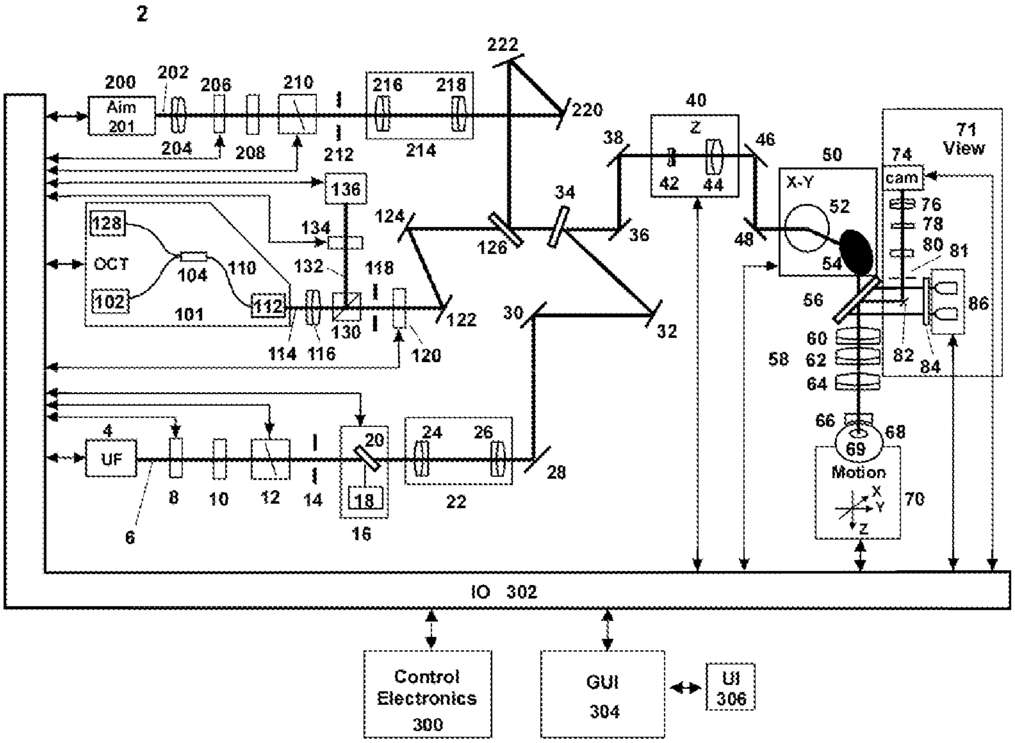
FIG. 3 shows a schematic representation of another embodiment of a system that can be used to perform a posterior capsulotomy and to perform surgery on an eye having a penetrated cornea.

Another alternate embodiment is shown in FIG. 3 and is similar to that of FIG. 1 but utilizes an alternate approach to the OCT 100. In FIG. 3, an OCT 101 is the same as the OCT 100 in FIG. 1, except that the reference arm 106 has been replaced by a reference arm 132. This free-space OCT reference arm 132 is realized by including a beam splitter 130 after the lens 116. The reference beam 132 then proceeds through a polarization controlling element 134 and then onto a reference return module 136. The reference return module 136 contains the appropriate dispersion and path length adjusting and compensating elements and generates an appropriate reference signal for interference with the sample signal. The sample arm of OCT 101 now originates subsequent to the beam splitter 130. Potential advantages of this free space configuration include separate polarization control and maintenance of the reference and sample arms. The fiber based beam splitter 104 of the OCT 101 can also be replaced by a fiber based circulator. Alternately, both the OCT detector 128 and the beam splitter 130 might be moved together as opposed to the reference return module 136.

Figure 4:
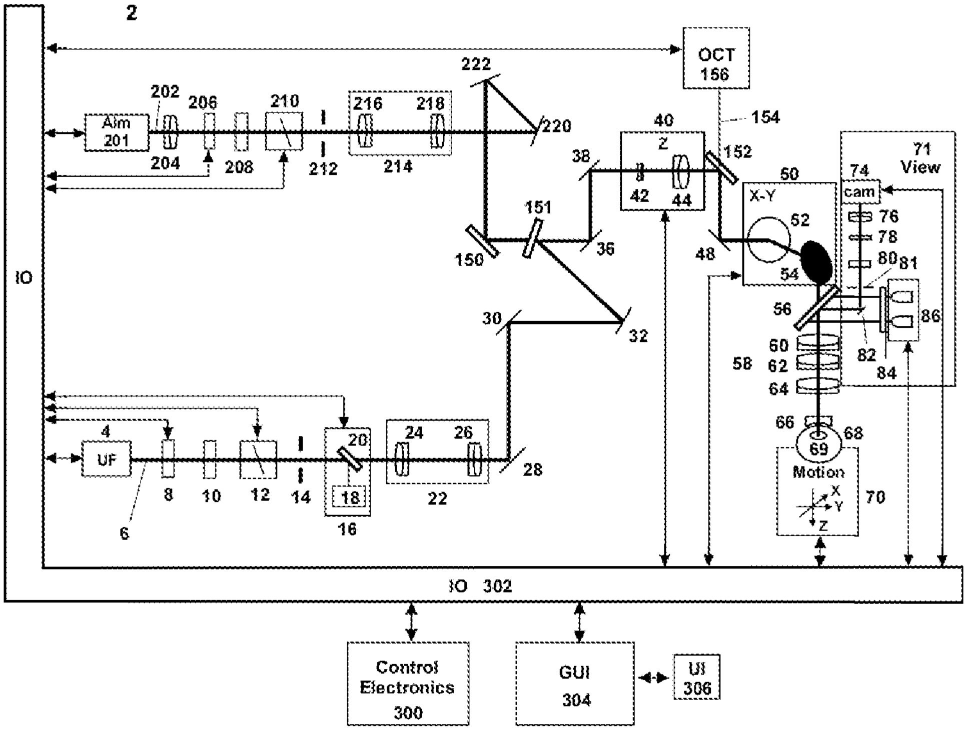
FIG. 4 shows a schematic representation of another embodiment of a system that can be used to perform a posterior capsulotomy and to perform surgery on an eye having a penetrated cornea.

FIG. 4 shows another alternative embodiment for combining the OCT beam 114 and the UF light beam 6. In FIG. 4, an OCT 156 (which can include either of the configurations of OCT 100 or 101) is configured such that an OCT beam 154 output by the OCT 156 is coupled to the UF light beam 6 after the z-scan device 40 using a beam combiner 152. In this way, the OCT beam 154 avoids using the z-scan device 40. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc, as described in U.S. Pat. Nos. 5,748,898; 5,748,352; 5,459,570; 6,111,645; and 6,053,613 (which are incorporated herein by reference.)

The system 2 can be set to locate the surface of the lens capsule and ensure that the light beam 6 will be focused on the lens capsule at all points of the desired opening. Imaging modalities and techniques described herein, such as for example, Optical Coherence Tomography (OCT), such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the anterior chamber and lens can be performed on the lens using the same laser and/or the same scanner used to produce the patterns for cutting. This scan will provide information about the axial location and shape (and even thickness) of the lens anterior and posterior capsule, the boundaries of the cataract nucleus, as well as the depth of the anterior chamber. This information may then be loaded into the laser 3-D scanning system or used to generate a three dimensional model/representation/image of the anterior chamber and lens of the eye, and used to define the patterns used in the surgical procedure.

Posterior Capsulotomy

In some instances, opacification of the lens posterior capsule occurs subsequent to the installation of an intraocular lens (IOL) in place of the natural lens. Posterior capsulotomy can be used to prevent vision degradation due lens posterior capsule opacification by removing the optically central portion of the lens posterior capsule, but is currently limited in application owing to the high level of difficulty involved in manual posterior capsulorhexis.

Figure 5:
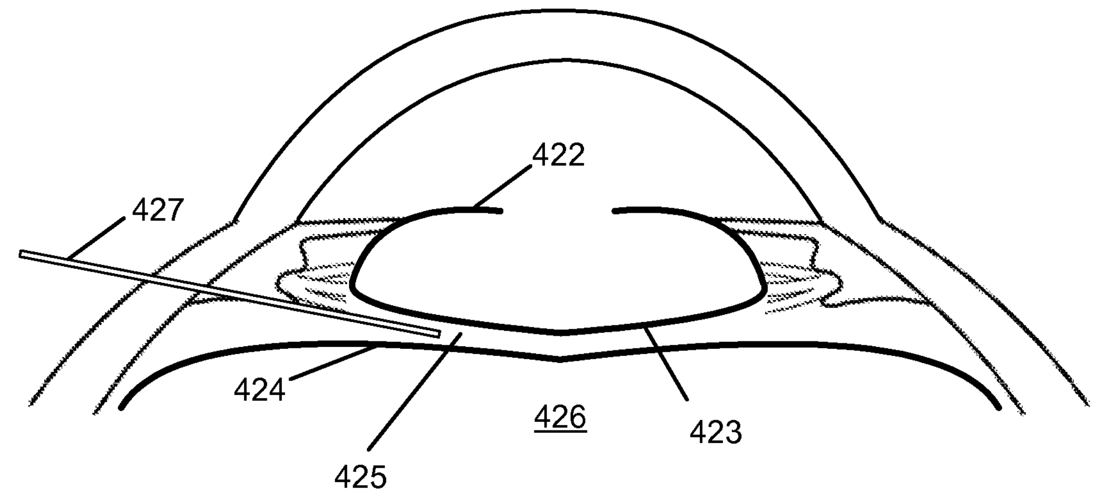
FIG. 5 is a cross-sectional diagrammatic view of a lens capsule and an adjacent portion of the anterior hyaloid membrane of the vitreous, in accordance with many embodiments.
Figure 6:
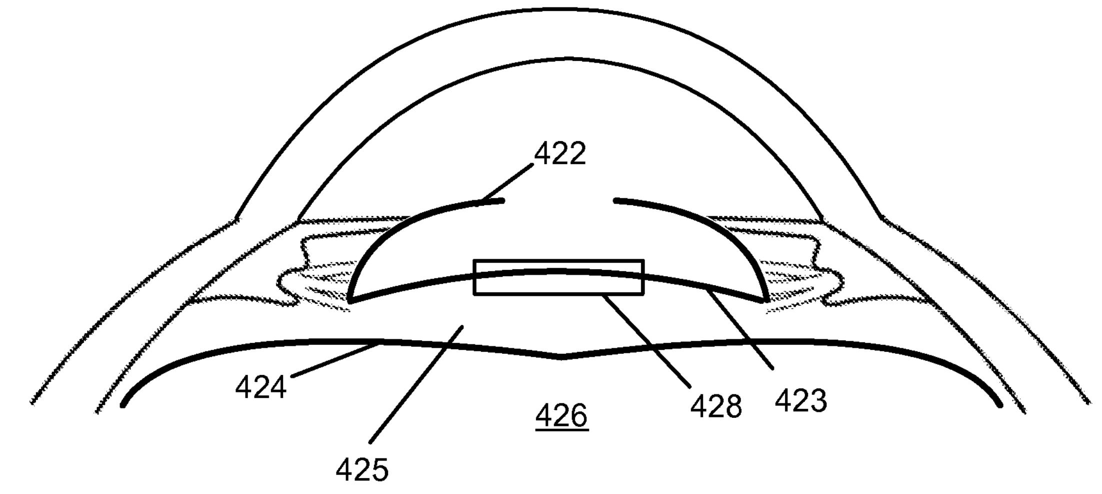
FIG. 6 is a cross-sectional diagrammatic view showing the lens posterior capsule inverted and displaced relative to the anterior hyaloid surface of the vitreous and a closed boundary incision surface transecting the lens posterior capsule, in accordance with many embodiments.

In many embodiments, the system 2 is configured to perform a posterior capsulotomy prior to IOL implantation. FIG. 5 illustrates an eye following anterior capsulotomy and lens removal. The lens posterior capsule surface of the empty lens capsule 422 is adjacent to a portion of the anterior hyaloid membrane 424 anterior to the vitreous 426. To avoid damage to the anterior hyaloid membrane 424 so as to avoid potentially compromising containment of the vitreous 426, the anterior hyaloid membrane 424 can be separated and displaced relative to the lens posterior capsule 423 using any suitable approach. For example, a suitable device (e.g. a 27 gauge self-bent needle 427) can be guided in a direction parallel to the lens posterior capsule surface 423 to create a small opening without touching the anterior hyaloid surface 424. A small amount of suitable fluid, such as an OVD, can be injected through this puncture into the Berger's space 425 behind the lens posterior capsule 423 and forward of the anterior hyaloid membrane 424, so as to elevate and separate the lens posterior capsule 423 relative to the anterior hyaloid membrane 424. FIG. 6 illustrates the lens posterior capsule 423 inverted in the anterior direction following injection of an OVD into the Berger's space 425.

An automatic 3D spectral domain OCT can then be performed as described herein to generate image data that can be processed by the system 2 to accurately measure the spatial disposition of the inverted lens posterior capsule and to characterize the size, shape, and dimensions of the corresponding anterior chamber. Such intra-operative OCT visualization can be accomplished just prior to and/or during laser incising of the inverted lens posterior capsule so as to accurately account for the spatial disposition of the inverted lens posterior capsule and/or the configuration of the anterior chamber as it exists during the incising of the inverted lens posterior capsule to accomplish the posterior capsulotomy.

The closed boundary incision surface 428 can be formed using any suitable system or method, including those described herein such as the system 2. For example, the closed boundary incision surface 428 can be formed using concurrent imaging as described herein to accurately locate the lens posterior capsule 423 as displaced from the anterior hyaloid membrane 424, so as to reduce the extent by which the closed boundary incision surface 428 extends on one or both sides of the lens posterior capsule 423 to reduce the probability of damaging the anterior hyaloid membrane. In many embodiments, system 2 is configured to generate surface definitions corresponding to intra-ocular tissue surfaces (e.g., lens anterior capsule, lens posterior capsule, corneal anterior surface, corneal posterior surface). The generated surface definitions can be depicted in conjunction with displayed OCT generated images of the intra-ocular tissues. For example, a cross-sectional display of an OCT generated image of intra-ocular tissues can be displayed with overlaid curves corresponding to the cross-section of the generated surface definitions for the anterior and posterior portions of the lens capsule. In many embodiments, the generated surfaces displayed on the OCT images can be adjusted by the system 2 so that the capsulotomy incision is positioned on the lens posterior capsule 423. The system 2 can be configured to set a suitable incision depth (e.g., 400 to 800 μm), a suitable pulse energy (e.g., 7 to 10 μJ), and a suitable capsulotomy diameter (e.g., at least 3.5 mm). After confirmation of the treatment zones, the laser application can be started. A suitable device, such as a micro forceps, can then be used to remove the lens posterior capsule disc without touching the intact anterior hyaloid surface.

The system 2 can also be used to perform a posterior capsulotomy before IOL implantation (no IOL in) without perforating the posterior capsulotomy with a needle. Such an approach can be used if there is a circumscript posterior capsular tear to prevent extension of the tear by performing a posterior capsulotomy without bringing the lens posterior capsule up into a convex shape. Such an approach can be used with an intact anterior hyaloid membrane as well as in case of vitreous prolapse.

Figure 7:
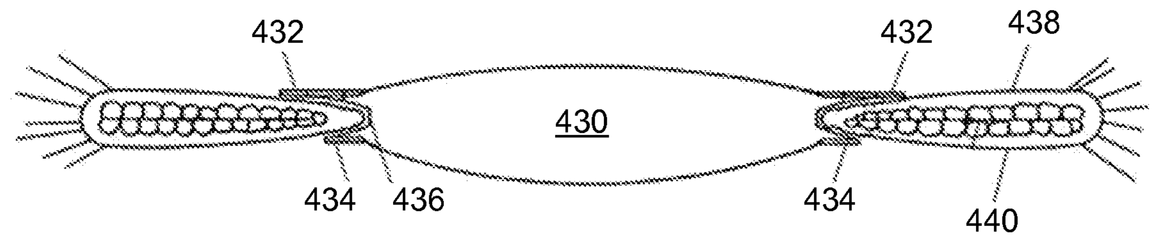
FIG. 7 is a cross-sectional diagrammatic view of an implanted bag-in-lens IOL, in accordance with many embodiments.

An IOL can then be installed by any suitable method. For instance, in accordance with a posterior optic buttonholing technique, an open-loop IOL can be implanted into the capsular bag. The optic can be buttoned-in by pressing down on the optic such that lens posterior capsule is anterior to the IOL and wraps around the periphery of the IOL optic between the haptic junctions. Alternatively, in accordance with a bag-in-the-lens technique, a suitable IOL (e.g., a BIL 89 A IOL) can be implanted such that the lens anterior capsule and the lens posterior capsule are placed in the flanks of the IOL optic. FIG. 7 is a cross-sectional view illustrating an implanted bag-in-lens IOL 430. The bag-in-lens IOL 430 has anterior flange 432 and a posterior flange 434 that extend around the perimeter of the IOL 430 thereby forming a retention groove 436 there between. The retention groove 436 accommodates the lens anterior capsule 438 having an anterior capsulotomy therein and the lens posterior capsule 440 having a posterior capsulotomy therein.

Posterior Capsulotomy with In-Situ IOL

Existing treatment of lens posterior capsule opacification subsequent to the installation of an IOL includes removal of the IOL to facilitate access to performing a posterior capsulotomy to remove a suitable portion of the opacified lens posterior capsule so as to provide a sufficiently sized optical pathway through the lens posterior capsule. In many embodiments, the system 2 is configured to perform a posterior capsulotomy through an IOL, thereby avoiding removal of the IOL. For example, the system 2 can use an optical beam having any suitable wavelength that is sufficiently transmitted through the IOL. While any suitable wavelength can be used, a wavelength between 320 nm to 430 nm may be beneficial by maximizing scattering of the electromagnetic radiation beam by the vitreous so as to minimize possible damage to the retina. The posterior capsulotomy can be performed after the surgical procedure used to implant the IOL is done and the access incisions through the cornea are closed/hydrated. The eye can be redocked to the system 2 and the system 2 used to laser incise the posterior capsulotomy without the need to open the eye again. Typically, the cut posterior capsule does not need to be removed as it disappears within hours latest because of inward rolling and contraction. It has been observed that a majority of eyes do not need any further injection or manipulation at all despite some little OVD or Optic ridge at the posterior optic or any other distance keeper behind the IOL optic. And sometime even this is not necessary. Iris hooks (with and without OVD) inserted from externally to internally can be used in order to dilate the pupil for subsequent lasing the posterior capsule.

Figure 8:
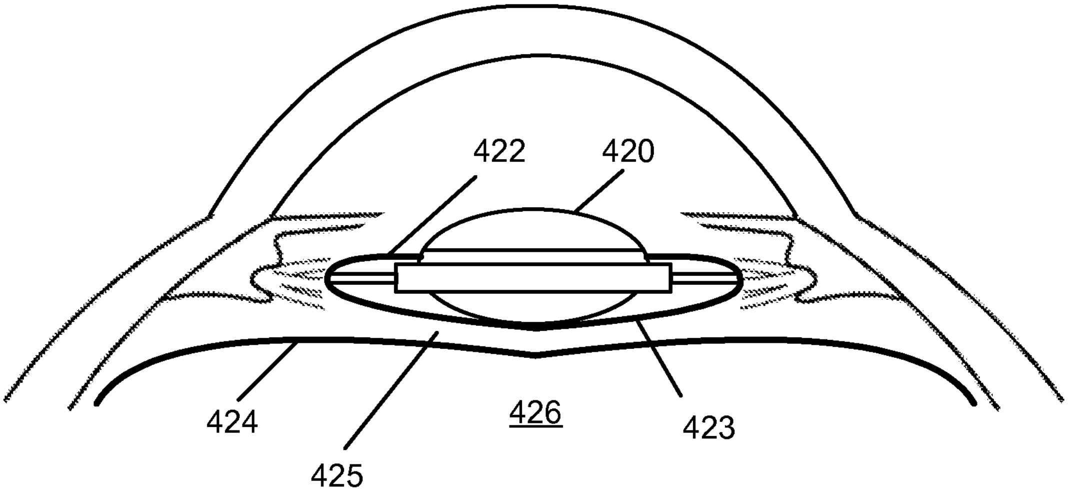
FIG. 8 is a side view diagram of an IOL positioned in a lens capsule and an adjacent portion of the anterior hyaloid membrane of the vitreous displaced relative to the lens posterior capsule, in accordance with many embodiments.
Figure 9:
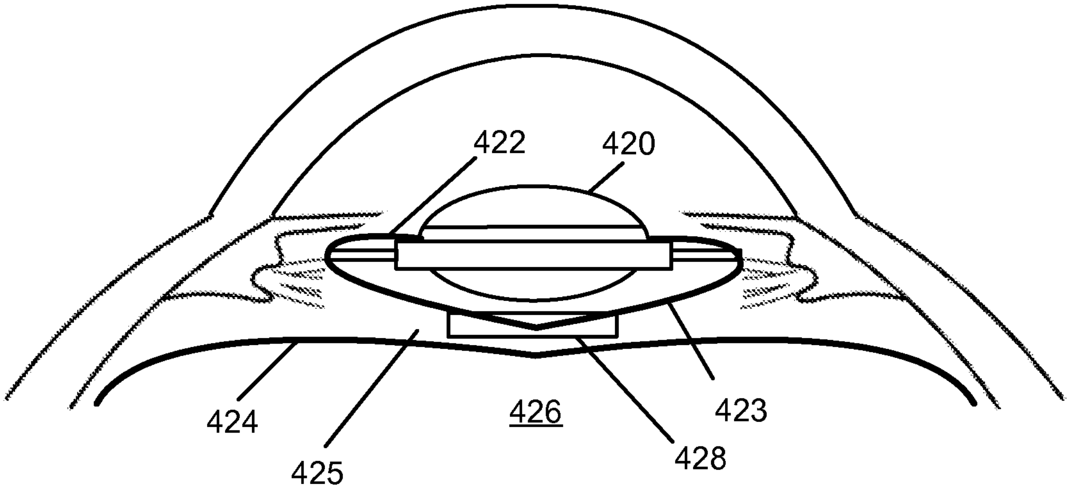
FIG. 9 is a side view diagram showing the lens posterior capsule displaced relative to the IOL of FIG. 8 and a closed boundary incision surface transecting the lens posterior capsule, in accordance with many embodiments.

FIG. 8 illustrates an IOL 420 positioned in a lens capsule 422 and an adjacent portion of the anterior hyaloid membrane 424 anterior to the vitreous 426. To avoid damage to the IOL 420 during posterior capsulotomy, the IOL 420 can be displaced relative to the lens posterior capsule 423 using any suitable approach. For example, a suitable device, such as a round blunt cannula, can be used to inject a small quantity of a suitable OVD homogeneously behind the IOL 420 and forward of the lens posterior capsule 423, such that the OVD spreads evenly behind to IOL 420 so as to separate the IOL 420 relative to the lens posterior capsule 423. FIG. 9 illustrates the adjacent portion of the lens posterior capsule 423 displaced relative to the IOL 420 and a closed boundary incision surface 428 transecting the lens posterior capsule 423.

An automatic 3D spectral domain OCT can then be performed as described herein to generate image data that can be processed by the system 2 to detect and identify the anterior and posterior surfaces of the IOL 420, the lens posterior capsule 423, and the anterior hyaloids membrane 424. The closed boundary incision surface 428 can then be formed using any suitable system or method, including those described herein such as the system 2. The closed boundary incision surface 428 can be formed using concurrent imaging as described herein to accurately locate the lens posterior capsule 423, the anterior hyaloid membrane 424, and the IOL 420 so as to reduce the probability of damaging the IOL and/or the anterior hyaloid membrane.

In many instances, the lens posterior capsule 423 is not connected to the anterior hyaloid surface 424. In many embodiments, the lens posterior capsule 423 can be seen on axial and/or sagittal OCT images between the posterior surface of the IOL 420 and the anterior hyaloid membrane 424 in the Berger's space 425. The incision depth can be set to a suitable range adapted to the size of the Berger's space 425 (e.g., between 400 μm to 800 μm). The system 2 can be configured to set a suitable pulse energy (e.g., between 7 μJ to 10 μJ) and a suitable capsulotomy diameter (e.g., at least 3.5 mm). For example, the system 2 can be configured to start the laser application in the Berger's space without cutting into the vitreous 426. After the laser treatment is finished, OCT imaging can be used to confirm that the free lens posterior capsule disc has fallen down onto the intact anterior hyaloid surface 424. The free lens posterior capsule disc may be seen as a triangle or square under an operating microscope. No further manipulations on the eye are necessary, as the lens posterior capsule disc can be moved out of the visual axis with minimal movement of the eye.

The system 2 can also be used to perform a posterior capsulotomy that results in intentional damage to the anterior hyaloids membrane. The resulting damage is very distinct and circumspect only. For example, in some instances, the lens posterior capsule 423 is directly attached to the anterior hyaloid membrane 424. The closed boundary incision surface 428 can be formed using concurrent OCT imaging as described herein. The system 2 can be configured after confirmation of the treatment zones to start the laser application in the vitreous 426 and then move in an anterior direction to incise the lens posterior capsule 423. The system 2 can be configured to set a suitable pulse energy (e.g., 7 to 10 μJ) and a suitable capsulotomy diameter (e.g., at least 3.5 mm). After the laser treatment is finished, in most cases the cut lens posterior capsule disc curls up and may be seen as a triangle or square lying on the anterior hyaloid surface 424. No further manipulations on the eye are necessary.

With an IOL already in place, the presence of the IOL may affect the precision and accuracy of the laser system. In many embodiments, the system 2 is configured to compensate for the presence of the IOL by using an index of refraction for the IOL to determine one or more control parameters used to control scanning of the focal point of the light beam 6. For example, the system 2 can be configured to receive a user input, for example, that specifies the index of refraction for the IOL used, or that is otherwise processed to determine the index of refraction for the IOL used. In many embodiments, the system 2 is configured to control the z-adjust device 40 and/or the scanning device 50 such that the scanning of the focal point of the light beam 6 is accomplished so as to account for any suitable combination of: 1) the optical characteristics of the IOL including the index of refraction of the IOL, 2) the configuration of the IOL, which can be measured by the system 2 using the approaches described herein, 3) the configuration of the anterior chamber, which can be measured by the system 2 as described herein, and 4) the optical characteristics of the fluid in the anterior chamber (e.g., the index of refraction of an OVD in the anterior chamber). For example, the index of refraction of the IOL, the measured configuration of the IOL, the measured configuration of the anterior chamber, and/or an index of refraction of the OVD in the anterior chamber can be used with known optical modeling methods (e.g., ray tracing) to suitably account for the configuration and optical characteristics of the anterior chamber and the IOL so as to accurately scan the focal point of the light beam 6 to incise the lens posterior capsule through the IOL in situ.

Anterior Capsulotomy with In-Situ IOL

The system 2 can also be used to perform an anterior capsulotomy with an in-situ IOL. For example, subsequent to IOL implantation in the capsular bag or ciliary sulcus, the system 2 can be used to create a perfect capsulotomy in case of a manual or too small capsulotomy for perfect covering capsule or a optic capture of the IOL posteriorly in case of a sulcus IOL implantation (for better fixation of the IOL, better centration, and prevention of anterior iris shafing).

OVD Compensation

Ophthalmic viscosurgical devices (OVDs) (also known as viscoelastic agents) comprise viscoelastic substances and can be used in eye surgeries. OVDs are transparent, gel-like substances that can be used during eye surgery in order to, for example, maintain and preserve space, displace and stabilize tissue, and coat and protect tissue. For example, in cataract surgery, the anterior chamber can be filled with an OVD to maintain the anterior chamber during capsulorhexis and IOL insertion, prevent iris prolapse and trapping nuclear fragments, and protect the corneal endothelium from turbulence, lens material, and/or ultrasound energy. The fluid in the anterior chamber can also be exchanged with a suitable OVD to provide a homogeneous optical medium in the chamber so as to enhance uniformity of transmission of the light beam 6 through the anterior chamber.

An increasing variety of OVDs are available. While many OVDs are composed of sodium hyaluronate, chondroitin sulfate, and methylcellulose, OVDs vary in molecular weights and viscosities. OVDs have properties of both fluids and solids and vary among each other with respect to viscosity, pseudoplasticity, viscoelasticity, and coatability. Suitable clinical applications for any particular OVD depend upon its characteristics.

Figure 10:
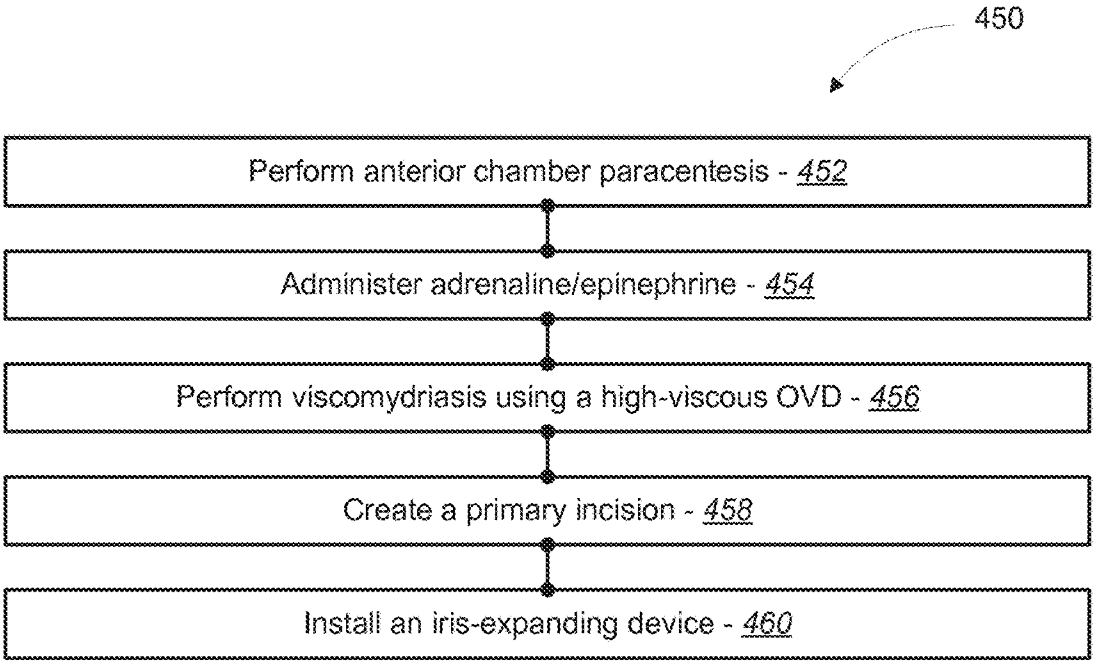
FIG. 10 is a simplified block diagram of acts of a method for installing an iris-expanding device, in accordance with many embodiments.

For example, a high-viscous OVD (e.g., sodium hyaluronate 2.3%) can be used in an approach to achieving pupil dilation adequate for cataract surgery (e.g., greater than 5 mm) in patients with small and/or non-dilating pupils. As illustrated in FIG. 10, viscomydriasis using a high-viscous OVD can be used as part of a method 450 to achieve adequate pupil dilation for small and/or non-dilating pupils. The method 450 includes performing anterior chamber paracentesis 452, administering adrenaline/epinephrine 454, performing viscomydriasis using high-viscous OVD 456, creating a primary incision 458, and installing an iris-exanding device (e.g., a Malyugin ring) act 460. Subsequent to the installation of the Malyugin ring, the patient's eye can be docked to the system 2 to laser incise the lens capsule and/or lens nucleus (e.g., anterior capsulotomy, lens fragmentation, posterior capsulotomy).

Figure 11:
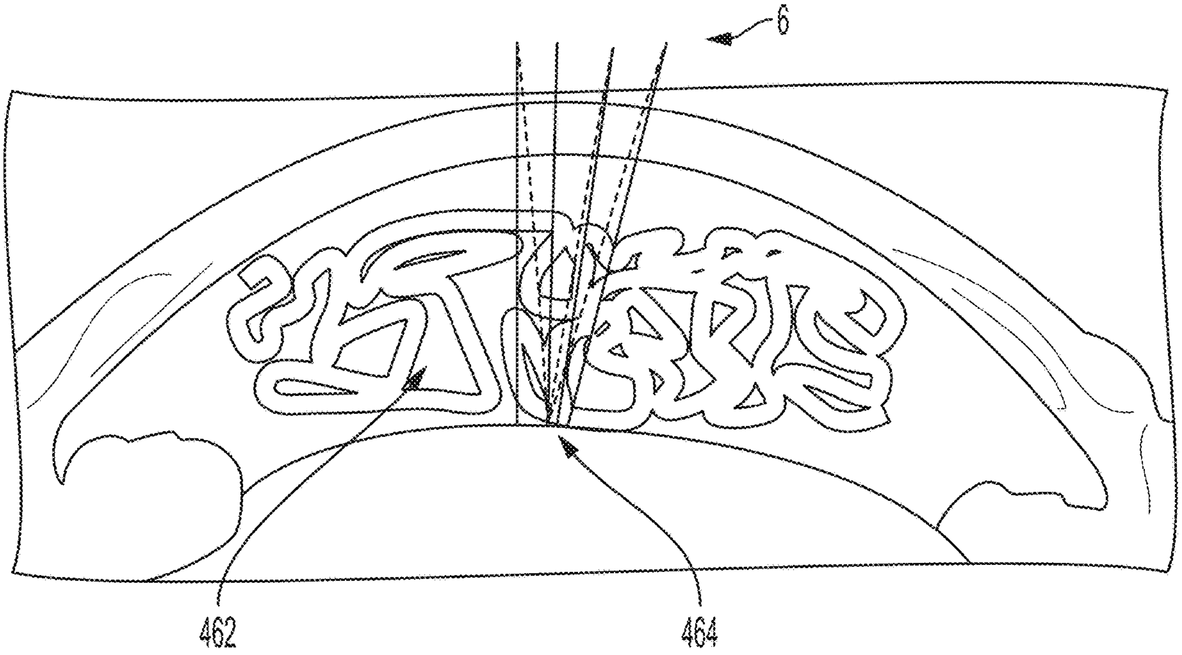
FIG. 11 is a cross-sectional diagrammatic view of an anterior chamber of an eye that contains an ophthalmic viscosurgical device (OVD) and how the refractive index of the OVD can impact the targeting of a laser beam transmitted through the OVD, in accordance with many embodiments.

The light beam 6 generated by the system 2 and used to incise the lens capsule and/or lens nucleus is transmitted through the OVD disposed in the anterior chamber. As a result, the optical characteristics (e.g., index of refraction) of the OVD in the anterior chamber impacts how the light beam 6 propagates through anterior chamber. As a result, the optical characteristics of the OVD 462 in the anterior chamber can result in distortion of the light beam 6 as illustrated in FIG. 11. For example, when the refractive properties of the cornea and the contents of the anterior chamber are accurately accounted for, the light beam 6 can be focused to a focal point that is accurately located, for example, to a focal point 464 that is accurately located relative to the lens anterior capsule. In contrast, if the refractive properties of the contents of the anterior chamber are not accurately accounted for, the light beam 6 may be focused to a focal point that is not accurately located, for example, to a focal point that is offset from the intended focal point 464. Also, the light beam 6 and imaging system may use light having different wavelengths, such that the adjustments to the targeted depth of light beam focal point can improve accuracy of the image guided treatment.

Accordingly, in many embodiments, the system 2 is configured to compensate for the OVD disposed in the anterior chamber by using an index of refraction for the OVD. For example, the system 2 can be configured to receive a user input that specifies the index of refraction for the OVD used, or that is otherwise processed to determine the index of refraction for the OVD used. The index of refraction for the OVD in the anterior chamber can then be used, in conjunction with the measured configuration of the anterior chamber, to control the z-adjust device 40 and/or the scanning device 50 such that the scanning of the focal point of the light beam 6 is accomplished so as to account for the presence of the OVD in the anterior chamber. For example, the index of refraction of the OVD in the anterior chamber and the measured configuration of the anterior chamber can be used with known optical modeling methods (e.g., ray tracing) to suitably account for the configuration and optical characteristics of the anterior chamber so as to accurately scan the focal point of the light beam 6 to incise the lens capsule and/or lens nucleus as desired.

Figure 12:
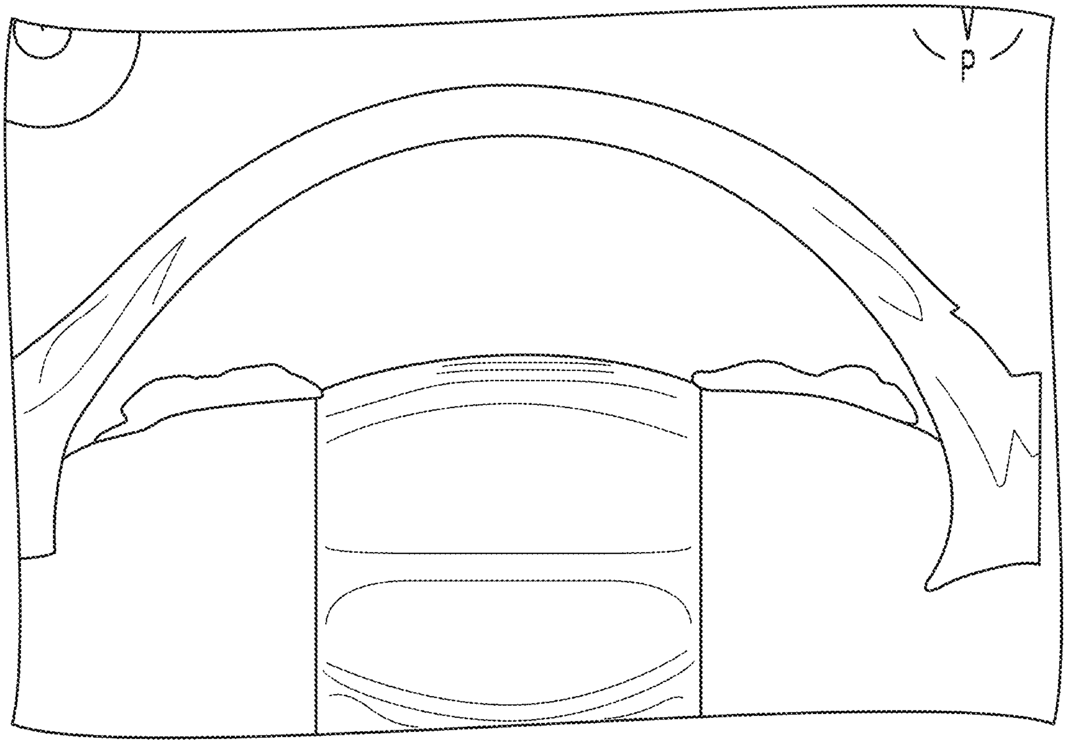
FIG. 12 shows a cross-sectional view image of an eye obtained via OCT imaging, in accordance with many embodiments.

As illustrated in FIG. 12, intra-operative OCT visualization can be used to generate image data that can be processed by the system 2 to characterize the size, shape, and dimensions of the anterior chamber, for example, when the anterior chamber is filled with the OVD. Such intra-operative OCT visualization can be accomplished just prior to and/or during laser incising of the lens capsule and/or lens nucleus so as to accurately account for the configuration of the anterior chamber as it exists during the incising of the lens capsule and/or lens nucleus.

Many suitable approaches can be used to process the OCT image data to characterize the size, shape, and dimensions of the anterior chamber. For example, the systems and approaches disclosed in U.S. Provisional Patent Application No. 61/722,080, entitled "Optical Surface Identification for Laser Eye Surgery", filed Nov. 2, 2012, and incorporated by reference herein in its entirety, can be used to generate a surface model of the posterior surface of the cornea and a surface model of the anterior surface of the lens, thereby characterizing the anterior and posterior surfaces of the anterior chamber.

Laser Surgery with a Penetrated Cornea

Figure 13:
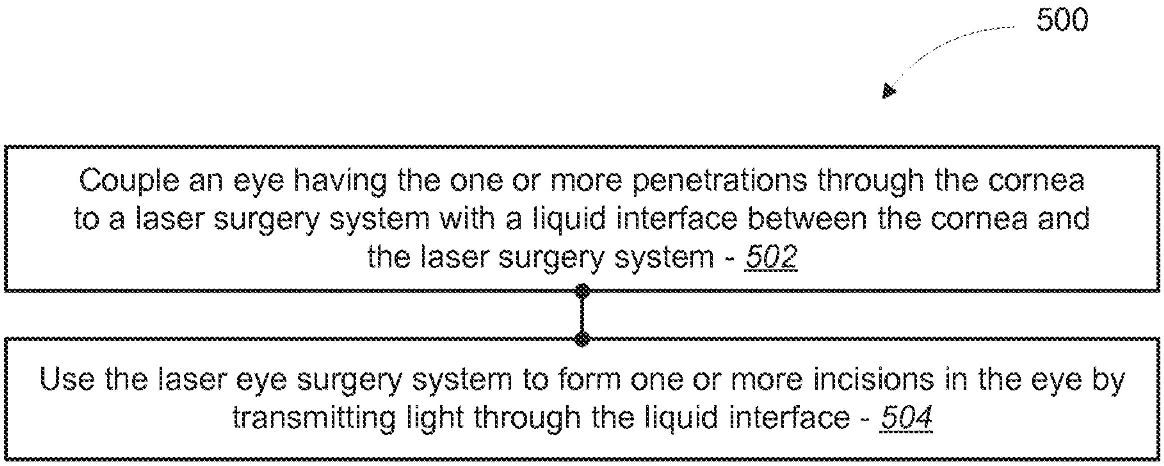
FIG. 13 is a simplified block diagram of acts of a method of performing laser eye surgery on an eye having one or more corneal penetrations, in accordance with many embodiments.

In many embodiments, the system 2 can be used for performing laser eye surgery on an eye having a penetrated cornea. For example, FIG. 13 shows acts of a method 500 for performing laser eye surgery on an eye having a penetrated cornea that can be accomplished using the system 2. One or more penetrations in a cornea of an eye may be formed to provide surgical access to the anterior chamber for performing a surgical act. The one or more penetrations can be formed in any suitable configuration using any suitable approach. For example, the eye can be coupled with the system 2 via the liquid optical interface 66 and the system 2 used to at least partially form the one or more penetrations in the cornea. The eye can then be decoupled from the system 2 so that a surgeon can perform a surgical procedure on the eye utilizing the one or more penetrations to access the interior of the eye. For example, the method 450 (illustrated in FIG. 10) can be performed utilizing the one or more penetrations so as to install an iris-expanding device to increase the portion of the cornea that can be laser incised by the system 2. In act 502, an eye having one or more penetrations through the cornea can be coupled to a laser surgery system (e.g., system 2) with a liquid interface (e.g., liquid optical interface 66) between the cornea and the laser surgery system. In act 504, the laser surgery system is used to form one or more incisions in the eye (e.g., anterior capsulotomy, posterior capsulotomy, one or more lens fragmentation incisions) by transmitting light through the liquid interface.

Figure 14C:
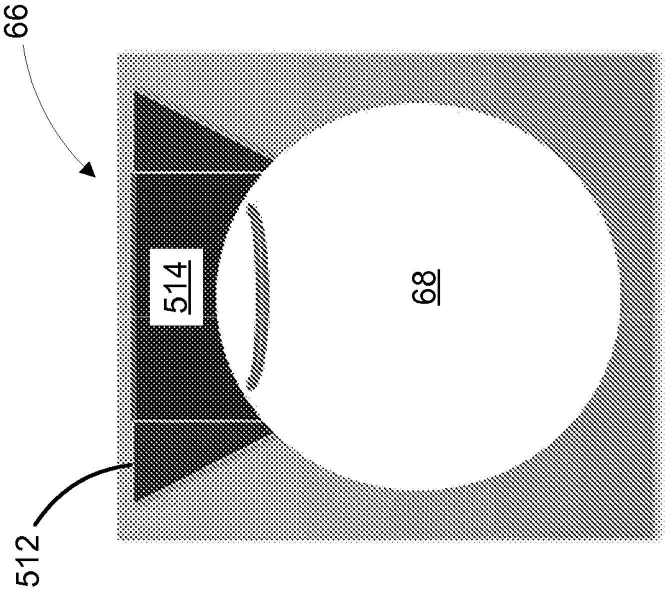
FIG. 14C is a simplified diagrammatic view of a liquid optical interface, in accordance with many embodiments, coupled to an eye.
Figure 14B:
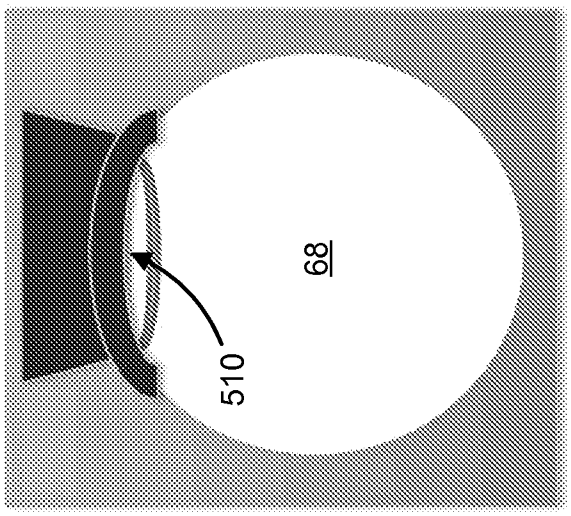
FIG. 14A and FIG. 14B are simplified diagrammatic views of flat and curved applanation interfaces, respectively, coupled to an eye.
Figure 14A:
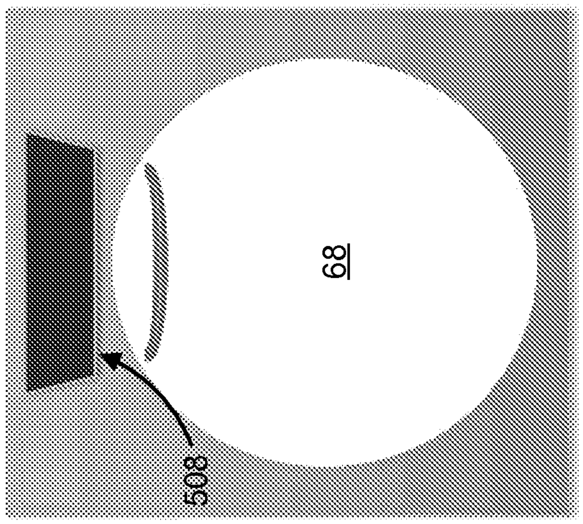

Advantageously, the liquid interface between the system 2 and the eye 68 avoids applying forces to the eye that would typically be applied by a hard surface interface between the system 2 and the eye 68. Applying such forces to the eye 68 may cause internal eye fluid to escape through the one or more penetrations in the cornea. For example, FIG. 14A illustrates a flat interface 508 that, when contacted with the cornea of the eye 68, can induce a substantial increase in intraocular pressure in the eye 68, thereby inducing internal eye fluid to escape through the one or more penetrations in the cornea of the eye 68. Even when a curved interface is used, such as the curved interface 510 illustrated in FIG. 14B, differences in curvature between the curved interface 510 and the cornea of the eye 68 and/or contact pressure between the curved interface 510 and the cornea of the eye 68 can induce a substantial increase in intraocular pressure in the eye 68, thereby inducing internal eye fluid to escape through the one or more penetrations in the cornea of the eye 68. In contrast, a liquid interface, such as the liquid optical interface 66 as illustrated in FIG. 14C, utilizes a liquid containment member 512 that can be coupled with the sclera of the eye 68 away from the limbus of the eye 68 via gentle suction, thereby avoiding inducing any substantial increase in intraocular pressure in the eye 68. The combination of the eye 68 and the liquid containment member 512 forms a reservoir for a liquid layer 514, which in many embodiments is exposed to the surrounding ambient pressure to avoid applying any significant pressure to the cornea of the eye 68 via the liquid layer 514. With the eye 68 coupled to the system 2 via the liquid optical interface 66, the light beam 6 generate by the system 2 is transmitted through the liquid layer 514 and into the eye 68. While not illustrated in FIG. 14C, in many embodiments the liquid optical interface 66 includes a disposable lens that is offset from the eye 68 such that the liquid layer 514 is disposed between the disposable lens and the cornea of the eye 68 and the liquid layer 514 is in contact with both the posterior surface of the disposable lens and the anterior surface of the cornea of the eye 68.

Figure 15:
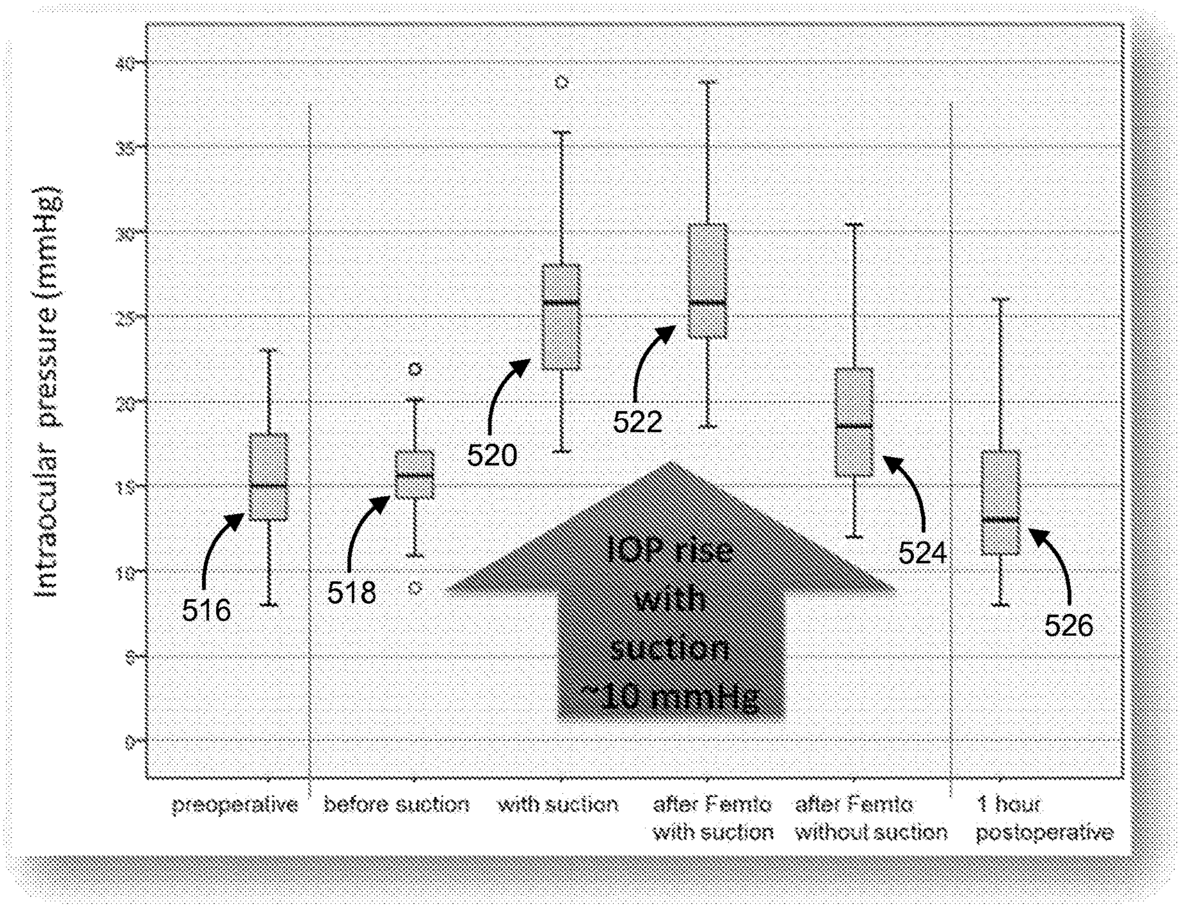
FIG. 15 is a chart presenting observed intraocular pressures before, during, and after surgery on eyes using an embodiment of a liquid optical interface.

FIG. 15 is a chart presenting observed intraocular pressure levels when using an embodiment of the liquid optic interface 66. The observed intraocular pressures include preoperative intraocular pressures 516, before suction intraocular pressures 518, with suction intraocular pressures 520, post laser incision with suction intraocular pressures 522, post laser incision without suction intraocular pressures 524, and one hour postoperative intraocular pressures 526. As shown, the with suction intraocular pressures 520, 524 are higher than the preoperative intraocular pressures 516 by approximately 10 mmHg.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for performing laser eye surgery on an eye having a cornea, the method comprising:
   - coupling an eye having a penetration through the cornea to a laser surgery system by using a liquid interface disposed between the cornea and the laser surgery system, wherein the penetration is pre-existing prior to the coupling and extends from an anterior surface of the cornea to a posterior surface of the cornea; and
   - forming one or more incisions in the eye by using the laser surgery system to transmit light through the liquid interface.

2. The method of claim 1, further comprising forming the penetration through the cornea.

3. The method of claim 1, further comprising inserting an iris expanding device through the penetration in the cornea.

4. The method of claim 1, wherein the one or more incisions in the eye include an anterior capsulotomy, a posterior capsulotomy, or one or more lens fragmentation incisions.

5. The method of claim 1, wherein the coupling of the eye to the laser surgery system by using the liquid interface includes:

coupling a liquid containment member of the liquid interface to a sclera of the eye away from a limbus of the eye via suction; and providing a liquid in a reservoir formed by a combination of the eye and the liquid containment member, wherein the liquid is exposed to a surrounding ambient pressure.

6. The method of claim 5, wherein the liquid interface further includes a disposable lens that is offset from the eye, and wherein the liquid is disposed between the disposable lens and the cornea of the eye and the liquid is in contact with both a posterior surface of the disposable lens and an anterior surface of the cornea of the eye.

* * * * *